(12) United States Patent
Gordon (10) Patent No.: US 8,318,090 B2
(45) Date of Patent: *Nov. 27, 2012

(54) HAND SANITIZER/STERILIZER (75) Inventor: Eugene I. Gordon, Mountainside, NJ (US)

(73) Assignee: Germgard Lighting, LLC, Dover, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,826

(22) Filed: Feb. 14, 2012

(65) Prior Publication Data

US 2012/0156094 A1    Jun. 21, 2012

Related U.S. Application Data

(63) Continuation of application No. 12/109,141, filed on Apr. 24, 2008, now Pat. No. 8,142,713, which is a continuation-in-part of application No. PCT/US2006/060263, filed on Oct. 26, 2006.

(60) Provisional application No. 60/730,677, filed on Oct. 26, 2005.

(51) Int. Cl.
| | |
|---|---|
| *A61L 2/00* | (2006.01) |
| *G05B 9/00* | (2006.01) |
| *B01J 19/08* | (2006.01) |
| *H01J 27/00* | (2006.01) |
| *G01N 21/00* | (2006.01) |
| *G01N 23/00* | (2006.01) |
| *A61N 5/00* | (2006.01) |
| *A61H 19/00* | (2006.01) |
| *A61M 35/00* | (2006.01) |
| *A61B 18/18* | (2006.01) |

(52) U.S. Cl. ....... 422/22; 422/24; 422/117; 422/186.05; 422/186.06; 422/1; 250/427; 250/432 R; 250/453.11; 250/455.11; 250/492.1; 250/492.3; 607/88; 607/94; 606/2; 606/11; 606/13; 606/32; 604/289; 604/292; 601/166; 601/DIG. 4; 601/DIG. 5

(58) Field of Classification Search ................. 422/1, 22, 422/24, 117, 186.05, 186.06, 906–907; 250/427, 250/432 R, 453.11, 455.11, 492.1, 492.3; 607/88, 94; 606/2, 11, 13, 32; 604/289, 604/292; 601/166, DIG. 4, DIG. 5
See application file for complete search history.

(56) References Cited

U.S. PATENT DOCUMENTS

| | | | | |
|---|---|---|---|---|
| 5,160,699 | A * | 11/1992 | Siegal | 422/24 |
| 6,343,425 | B1 * | 2/2002 | Sias et al. | 34/389 |
| 8,142,713 | B2 * | 3/2012 | Gordon | 422/22 |

* cited by examiner

*Primary Examiner* — Jill Warden
*Assistant Examiner* — Monzer Chorbaji
(74) *Attorney, Agent, or Firm* — Wolff & Samson PC

(57) ABSTRACT

Disclosed are a germicidal system and method for deactivating pathogens on the surface of a bodily extremity protected by a prophylactic covering substantially opaque to UV-C radiation. The device includes an enclosure having one or more openings through which the extremity can be inserted. The enclosure contains a radiation source configured to produce germicidal radiation having a wavelength of about 253.7 nm. The openings are configured relative to the radiation source such that the inserted extremity is in close proximity to the radiation source. The prophylactic covered extremity is preferably a gloved hand thereby sanitizing the surface of the glove. The extremity inserted is preferably exposed for a predetermined period of time to ensure a desired level of sanitization. Optionally, the device can include detectors to determine the position of the hand, the spread of the fingers, and whether the hand is covered by a glove.

28 Claims, 3 Drawing Sheets

HAND SANITIZER/STERILIZER

This application is a continuation of prior application Ser. No. 12/109,141 filed on Apr. 24, 2008, which claims priority pursuant to 35 U.S.C. §120 and §363 from International Patent Application Serial No. PCT/US06/60263 entitled "Hand Sanitizer," having an International Filing Date of Oct. 26, 2006, which claims priority from U.S. Provisional Application Ser. No. 60/730,677 filed on Oct 26, 2005, all of which are herein incorporated by reference in their entirety.

FIELD OF THE INVENTION

This invention relates to a germicidal device having germicidal properties, and more particularly to a germicidal device having a UV-C radiation source that deactivates pathogens on the surface of bodily extremities inserted into the device.

BACKGROUND OF THE INVENTION

Infectious diseases are caused by various pathogens: virus, bacteria, fungus, spores, etc. Once on or within the body they replicate and ultimately can cause infection and illness, sometimes resulting in death. Pathogens reach the body through contaminated food, aerosolized pathogens in air or on dust, human contact with surfaces or human-to-human contact. Hands are a significant vehicle for disease transmission. Thus, hand washing is one important means of preventing the spread of infection and germs that can cause colds and flu.

In a hospital or other health care environment health care workers and physicians are significant factors in disease transmission from patient to patient by virtue of inadequate attention to, or inadequate technology for, hand sanitation. Sanitation is defined as a reduction of pathogens of any given type by a factor of $10^4$. The traditional method of sanitizing hands is hand washing with soap or anti microbial soap and drying with sterilized towels. Recently, the application of alcohol formulations followed by a short drying period has become a common hand sanitizing process. Hand washing, possibly including the forearms, is capable of removing a fraction of the transient pathogens, and alcohol rubs kill many but not all types of pathogens. However, each technique has inadequacies in that elimination or reduction by a factor of $10^4$ of active pathogens is not always complete or assured, does not cover 100% of the area to be sanitized and not always possible for multiple reasons. The result is variable; there is no certainty in any particular instance.

Extended application time improves the protection. For example, surgeons scrub for many minutes to improve the removal of pathogens, and nurses and other healthcare workers wash their hands frequently, and as a result, cause their hands to become painfully sore thereby making it difficult to use the technique consistently. Thus, as the required application time increases and the unpleasant side effects increase, compliance with sanitization procedures decreases. Surgeons may not scrub for the necessary length of time—approximately 10 minutes—or with the necessary vigor, and nurses may avoid hand washing to reduce the discomfort associated with the hand irritation that can be exacerbated by wearing latex gloves. Moreover wearing latex gloves does not solve these problems. As health care professionals go from patient to patient, they can transport pathogens on the surfaces of the gloves just as they can on bare hands. Furthermore, one touch of any surface by the hand contaminates the hand. All the effort at sanitation can be lost by a single touch by the hand of a surface or by settling of aerosols containing pathogens or dry pathogens drifting in the air. The contaminated hand is a major vehicle for transmission of pathogens to the patient and possibly the primary source of hospital acquired infection spread. Furthermore, the gloves cannot be easily washed while being worn, the gloves are not replaced as often as should be to limit the transmission of disease and constant replacement of gloves increases costs associated with patient care. It is generally understood that the purpose of the gloves is to protect the healthcare worker from the patient, not the patient from the healthcare worker.

The necessary time for effective use of alcohol including drying is tens of seconds. One factor that is cited as a significant inconvenience is the time required to achieve substantial reduction of the number of pathogens (e.g., 99.99%), or missed areas and thus the process of sanitation is frequently bypassed. Alcohol rubs are ineffective on spores. Another factor is that the use of alcohol dries the epidermis, which is supposed to function to protect the moisture of the skin. Hence the skin sometimes can become irritated and the procedure is bypassed.

Bare hands are also a major element in the spread of infection in schools. The cost to schools of absence is very high. Students can miss class time and carry illnesses home. Hence, proper hand sanitation in the school environment is also financially important to the schools, to the students and to the parents. Washing hands is typically not practiced as frequently as desired or in a sufficient manner. Moreover, in many developing countries, the sanitary and hygienic conditions at schools are often very poor, and can be characterized by the absence of properly functioning or existing water supply for sanitation or hand washing facilities. Studies have demonstrated that the absentee rate is reduced by 50% with proper hand washing.

Clean hands in restaurant settings are similarly critical to prevent the spread of disease. The FDA reports that poor personal hygiene in a food service environment is a critical area that needs immediate attention and makes the following points with respect to personal hygiene: proper, adequate hand-washing, prevention of hand contamination, good hygienic practices, hand-washing facility, convenient/accessible, and hand-washing facility, cleanser/drying device.

A summary of several studies and initiatives concerning hand-hygiene can be found in an article by Kelly M. Pyrek, entitled "Hand Hygiene: New Initiatives on the Domestic and Global Fronts," published on Jun. 1, 2006, and available at a web site maintained by Infection Control Today (ICT), the entire disclosure of which is hereby incorporated by reference.

Ultra-violet germicidal irradiation (UVGI) can be use to deactivate pathogens such as anthrax, smallpox, viral hemorrhagic fevers, pneumonic plague, glanders, tularemia and drug resistant tuberculosis. Pathogens that have a relatively thick cell wall, such as spores, are more resistant to UVGI because the cell wall is not easily penetrated. However, with greater intensity and longer exposure times, even the more resistant pathogens are deactivated by UVGI.

The effectiveness of UVGI derives from a band of UV-C radiation centered at a wavelength of 265 nm plus or minus 30 nm. The UV-C radiation modifies the DNA and eliminates the ability of a pathogen to reproduce. Pathogens that can't reproduce are not infectious, and are therefore harmless. Germicidal reduction of the density of reproducing pathogens in air is based on the ability of UV-C radiation, from an emitted spectral line of mercury excited by a low pressure gas discharge, typically in argon, centered at $\lambda 253.7$ nm, to eliminate the ability to reproduce of a percentage of pathogens of a given type in the air surrounding the tube. Other types of tubes are capable of producing radiation in the UVGI band, for example xenon discharge tubes (see e.g., http://xingguang.en.alibaba.com/group/200028075/Xenon_lamp.html). The percentage depends on the product of UV-C intensity at the pathogen and exposure time, typically called the dose.

Radiation intensity is a measure of radiant power incident per unit area. If a pathogen is in the presence of germicidal radiation of a given wavelength for a given exposure time, the integral of the radiation intensity experienced by the pathogen over time determines the radiant exposure per unit area or dose. The surface area of the pathogen defines the actual energy incident on the pathogen. Some of the incident energy is absorbed, which results in the deactivation of the pathogen. Deactivation is also referred to as inactivation.

A study by P. W. Brickner et al. discusses the duration and intensity of exposure to radiation having a wavelength of 253.7 nm that is required to deactivate various pathogens. See P. W. Brickner, R. L. Vincent, M. First, E. A. Nardell, M. Murray, and W. Kaufman, "The Application of Ultraviolet Germicidal Radiation to Control Transmission of Airborne Diseases: Bioterrorism Countermeasure," PUBLIC HEALTH REPORTS, Vol. 118, pp. 990-114, March-April 2003 (available at http://www.publichealthreports.org/userfiles/118_2/118099.pdf) (hereinafter, "the Brickner study").

The following table includes a sample of the data presented in the Brickner study. The table describes the average flux used in the experiment not the actual absorbed energy. Differences reflect both different size of the pathogen and different required dose.

Examples of actinic exposure data for 90% reduction in colony formation

| Microorganism | Required Radiant Exposure for 90% Deactivation (J/m$^2$) | Type |
| --- | --- | --- |
| Streptococcus (various) | 18.4 to 61.5 | Bacteria |
| Tubercle bacillus | 100.0 | Bacteria |
| Bacillus anthracis | 45.2 | Bacteria |
| Salmonella tiphi | 21.4 | Bacteria |
| Dysentery bacilli | 22 | Bacteria |
| Micrococcus luteus | 197 | Bacteria |

Deactivation to 99% requires twice the radiant exposure for 90% deactivation. Sanitation or 99.99% deactivation requires four times the radiant exposure. Hence for Tubercle bacillus sanitation requires a radiant exposure of 400 J/m$^2$. If the intensity at a surface is 500 watts/m$^2$ the time required for sanitation of the surface for the particular bacteria is 0.8 seconds.

UVGI has not been employed as an alternative to soap or alcohol based hand sterilization since it cannot be used on bare skin. What is needed in the art is a system and method for effectively sterilizing hands using UVGI that avoids the negative side effects of traditional hand sanitation and more particularly a method and system for sterilizing gloved hands.

SUMMARY OF THE INVENTION

In accordance with one aspect of the present invention, a germicidal device for deactivating pathogens on the surface of a bodily extremity, such as a hand and forearm, inserted into the device is presented. The device includes a radiation source configured to produce radiation having a wavelength of about 253.7 nm. The radiation source is contained within an enclosure having one or more openings that allow insertion of the extremity into the enclosure such that the extremity is in close proximity to the radiation source. Furthermore, the enclosure may include a locking device that closes down on the inserted body part. The locking device has at least two functions: to prevent premature withdrawal before sanitation or sterilization is complete; and to prevent UV-C from escaping from the enclosure.

In accordance with a further aspect of the present invention, the radiation source contained in the enclosure produces about 500 Watts/meter$^2$ near a surface of the radiation source. A feature of the invention is the distribution of sources and the use of aluminum surfaces within the box to provide high reflectivity for the radiation. This produces a uniform, isotropic radiation intensity.

In yet a further aspect of the present invention, a method for sanitizing a hand and/or forearm using UV-C radiation is presented. One or more UV-C radiation sources having a wavelength of about 253.7 nm contained within an enclosure are activated. The hand and/or forearm to be sanitized is inserted into the enclosure through one or more openings such that the hand and/or forearm is in close proximity to the surface of the UV-C radiation sources. The hand and/or forearm is then exposed to the UV-C radiation for a predetermined period of time.

In yet a further aspect of the present invention, the germicidal device includes a surface detector that identifies whether the bodily extremity inserted into the device is covered, e.g., a gloved hand, or has exposed bare-skin. Since prolonged exposure to UV-C radiation can be harmful to skin, this feature can protect against unintentional operation of the device or prolonged exposure to bare skin.

In yet a further aspect of the present invention, the germicidal device includes a spread finger detector that ascertains the positioning of the hand and/or forearm. This feature also detects the positioning of the fingers, ensuring that sufficient spacing exists so that shadows are minimized and exposure to the UV-C radiation everywhere on the glove including between the fingers is maximized.

In yet a further aspect of the present invention, in situations where the bodily extremity is a gloved hand, a user may use a glove that includes a reflective coating on its surface, for example a thin film of aluminum, in order to maximize UV-C exposure to the pathogens. A glove coated in reflective material increases the effective UV-C exposure, making the germicidal device more effective.

The features of the present invention allow for the sterilizations to be completed in a short time. Since hands are constantly contaminated through the touch of any surface, the handling of an instrument, or the settling of aerosols containing pathogens, the short time required to complete a sanitation or sterilization allows for repetitive use so that the hands can be repeatedly sterilized or sanitized between every interaction with a patient during a single patient visit.

In use one must block all UV-C radiation from leaving the enclosure. Thus, the entrance contains an opening that is closed down on the forearm during the exposure period and then opens after exposure to allow removal of the gloved hand without recontamination.

These and other aspects, features and advantages will be apparent from the following description of certain embodiments and the accompanying drawing figures.

BRIEF DESCRIPTION OF THE DRAWINGS

The foregoing and other features of the present invention will be more readily apparent from the following detailed description and drawings of the illustrative embodiments of the invention wherein like reference numbers refer to similar elements throughout the views and in which.

DETAILED DESCRIPTION OF CERTAIN PREFERRED EMBODIMENTS

By way of overview and introduction, the present invention comprises a germicidal device that can provide the rapid and effective sterilization of hands, and other bodily extremities, in many locations including schools, childcare centers, hospitals and other medical offices, restaurants and kitchens, bathrooms, supermarkets, homes, and public facilities. The germicidal device preferably includes an enclosure, such as a device, mounted to a wall or otherwise elevated, for example by a patient bed, table, stand or sink. The enclosure contains a radiation source configured to produce UV-C radiation preferably having a wavelength of about 253.7 nm. The enclosure further includes an opening (e.g., a slot) through which an extremity, such as hands, or hands and forearm, can be inserted into the device and exposed to the UV-C radiation thereby deactivating the pathogens on the surface of the user's hands. Optionally, the germicidal device can be used with uncovered bodily extremities, such as bare hands, to deactivate the pathogens on the surface. However, exposure to bare skim must be limited since UV-C exposure is regulated. Typical exam or surgical gloves are substantially opaque to the radiation, hence the system may be used beneficially and without substantial risk for sanitizing or sterilizing gloved hands. Accordingly, a preferred embodiment of the present invention includes the sanitation or sterilization of covered body parts since coverings such as latex or nitrile gloves are substantially opaque to UV-C radiation.

Figure 1:
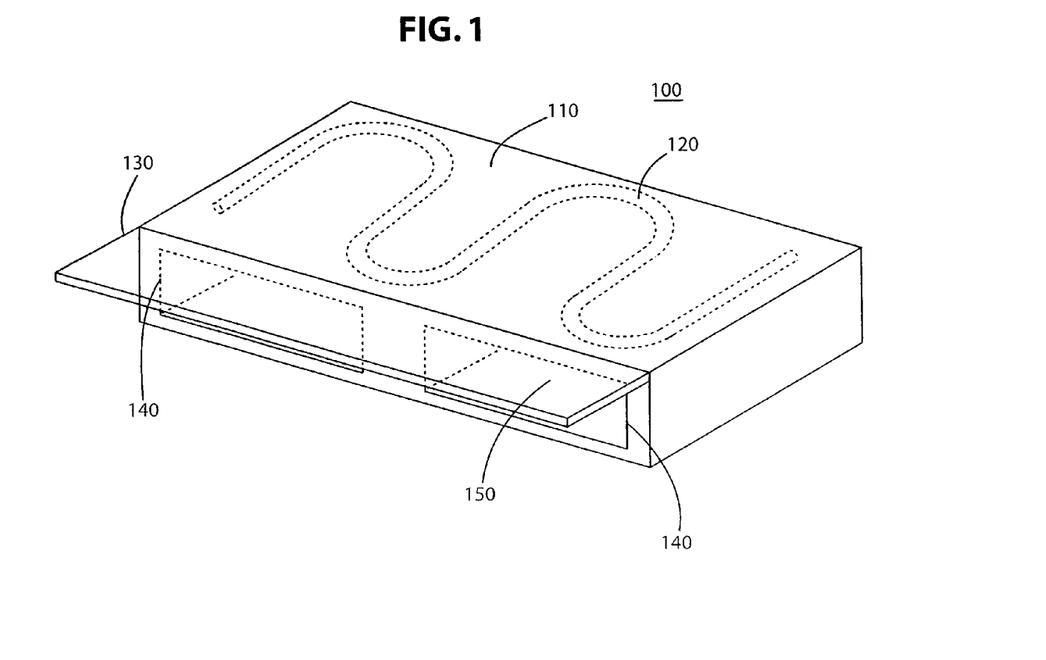
FIG. 1 illustrates an embodiment of a germicidal device in accordance with the present invention.

With reference now to FIG. 1, the germicidal device 100 is illustrated in accordance with one embodiment of the present invention. The germicidal device 100 includes an enclosure 110 that houses a radiation source 120 capable of producing UV-C radiation in the required band. The enclosure 110 includes at least one variable opening 140 for insertion of bodily extremities into the device. While the invention is discussed below with respect to the sanitization of a user's hands, it would be appreciated by one of skill in the art that the user may insert more than just hands, including forearms, or whatever length of arm that may fit into the enclosure 110.

The embodiment illustrated in FIG. 1 includes two openings 140, each of which is suitable for insertion of a user's outstretched hand, and optionally, a portion of the user's wrist and forearm, into the enclosure 110. Alternatively, the enclosure 110 can include one opening 140 for sequential exposure of the user's hands, or if the opening is large enough, concurrent exposure of multiple hands. Multiple openings 140 can also be included for environments in which it may be beneficial to allow multiple simultaneous users, such as public restrooms or large kitchen facilities. A germicidal device 100 including multiple openings 140 can further include multiple radiation sources 120 configured to irradiate the area surrounding only those openings 140 being used.

Figure 2:
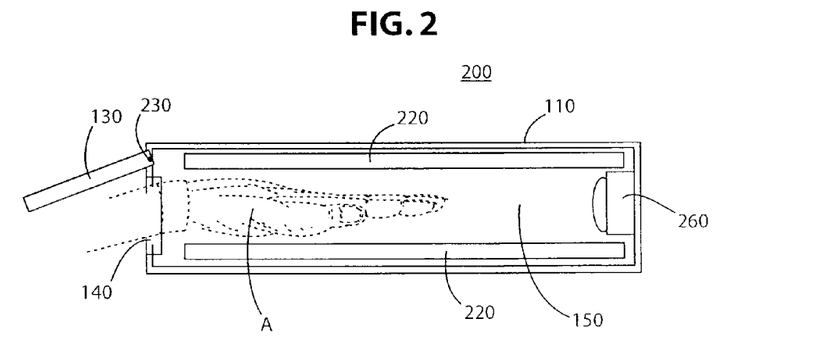
FIG. 2 illustrates a further embodiment of a germicidal device in accordance with the present invention.

The enclosure 110 illustrated in FIG. 1 illustrates a single radiation source 120 that includes U-shaped sections to irradiate the inside of the enclosure 110. The number, configuration, and geometry of the radiation sources 120 within the germicidal device 100 can be varied to suit the geometry of the enclosure 110 and its intended use. Multiple U-shaped tubes or multiple linear tubes can be used as radiation sources 120. Additionally, while FIG. 1 illustrates a single curved tube on the top surface 150 of the inside of the enclosure, optionally, as illustrated in FIG. 2, radiation sources 220 can be placed in multiple locations, including top and bottom interior surfaces 150, side interior surfaces 150, or spanning interior surfaces 150 (e.g., a linear tube connected to the top surface and the bottom surface.

The radiation source 120 may consist of an argon mercury discharge lamp housed in a quartz or borosilicate glass tube. Both quartz and borosilicate are chosen so that the absorption of the radiation at 253.7 nm by the envelope is minimized. Although the optical performance of quartz is generally better than that of borosilicate glass, production costs associated with borosilicate glass can be lower than that of quartz. Quartz tubes are typically made by hand whereas borosilicate tubes can be fabricated by automated equipment.

In a further feature of the present invention, the interior surface 150 of the enclosure 110 can reflect UV-C radiation to increase the radiation intensity within the enclosure. Reflective interior surfaces 150 can decrease the number of required UV-C radiation sources and decrease the complexity of the geometry of the radiation sources 120. Furthermore, reflective surfaces can increase the radiation intensity in crevices or irregularities in the hands inserted into the enclosure 110, such as between the fingers. Furthermore, the reflective surfaces may ensure that an approximately uniform intensity isotropic radiation is produced within the enclosure 110.

Figure 3:
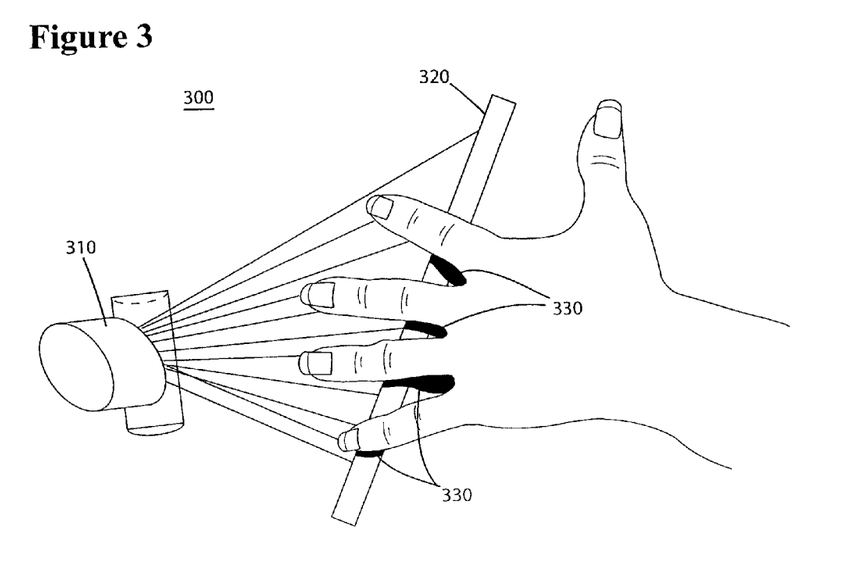
FIG. 3 illustrates a spread detector according to an aspect of a germicidal device of the present invention.

In a further feature of the present invention, the germicidal device 100 can include a spread finger detector 300 as shown in FIG. 3. The spread finger detector ensures that a bodily extremity (e.g., hands and fingers) is optimally or properly positioned within germicidal device 100. In an embodiment where the bodily extremity being sanitized is a hand, optimal positioning may include proper insertion of the hand itself and sufficient spacing between fingers. Proper positioning increases the coverage of UV-C exposure in crevices, wrinkles, and irregularities of the hands, especially in areas such as between fingers, making the germicidal device 100 more effective. The spread detector 300 may include a processing unit (not shown), a source 310, and a detection array 320, which is preferably positioned opposite the source 310. Source 310 may consist of a light emitting diode ("LED") and a lens. The lens of source 310 can create an elliptical illumination pattern from the light emitted by the LED. The elliptical illumination can be focused across the inserted fingers of the gloved hand to be sterilized, with the long axis of the ellipse perpendicular to the fingers. Detection source 320 may consist of a photodiode array, or an array of any photo-detection devices. As the source 310 illuminates the hand, the detection array 320 will capture the light emitted by the source 310. Portions of the detection array 320 that are under the shadow of the hand 330 will receive a reduced intensity of light from the source 310 relative to the portions of the detection array 320 that are not blocked by the hand from the light emitted by the source 310. The pattern captured by the detection array 320 creates a "map" of the hand position, including the spread of the fingers. This "map" is then analyzed according to algorithms stored in the processing unit to determine whether the hand is optimally positioned. The algorithms defining optimal positioning may include parameters that measure sufficient spreading of the fingers. Additionally, the spread detector 300 may include indicators (not shown) to show when the bodily extremity is in an optimal position. The indicators (not shown) may include lights, or an audible signal. Furthermore, when using the germicidal device 100, the user can rotate the hands within the enclosure 110 to increase exposure to all surfaces of the hand. Additionally, the user can turn the fingertips up (or down) so as to face the radiation source 120 and expose the space between the nails and fingers to high intensity UV-C radiation. Preferably, rings, bracelets, wristwatches, and other jewelry are removed to insure that pathogens under the jewelry are deactivated.

UV-C radiation having a wavelength of 253.7 nm produced by the radiation sources 120, and optionally reflected by the interior surface 150, of the enclosure generally causes no significant damage to human skin. The outer layer of the skin, part of the epidermis, is about 20 microns thick, and serves to protect the layers underneath. It is a barrier layer providing physical protection for the critical layers underneath (dermis) and inhibits water loss to the outside from the underlying layers. It has no blood supply, and therefore has no ability to reproduce. It provides no excretions needed by the skin and has a total lifetime of about 30 days before desquamation.

The absorption depth of the outer layer for 253.7 nm wavelength radiation is about 3 microns, and most of the radiation is absorbed in the surface layer of the epidermis (i.e., the stratum corneum). The fraction of radiation transmitted to the dermis is approximately 0.001. Thus, UV-C radiation having a wavelength of 253.7 nm is inconsequential to the health of the skin because of the structure of the epidermis and because the stratum corneum quickly sloughs off.

Thus, the absorption depth in the skin is so small that any damage is superficial. However, excessive exposure can cause erythema, a reddening of the skin. Additionally, OSHA and other organizations establish UV-C exposure limits. Hence, there are limits on how often the device should be used on bare-hands. Accordingly, for bodily extremities such as hands, gloves provide a measure of protection against UV-C radiation. The thickness of a glove is generally much greater than the penetration depth of UV-C. Additionally, gloves made from materials with optical characteristics that make them substantially opaque to UV-C may provide enhanced protection against UV-C radiation. For example, latex and nitrile, materials which are typically used to manufacture surgical/exam gloves, exhibit high optical loss, providing further protection for the hands. Accordingly, one variation of use of the germicidal device 100 includes the sterilization of gloved hands. In addition to protecting the hands from excessive UV-C exposure, some environments require the user to wear a glove (e.g., latex gloves), such as in a kitchen or in a hospital or other medical facility. These environments require frequent and rapid sterilization, which is typically accomplished by removing the contaminated gloves and placing a new pair of gloves on the user's hands. As noted, the germicidal device 100 provides an effective, quick, and cost-saving alternative to constantly replacing gloves. The user can insert the gloved hands into the enclosure 110 to sanitize the surface of the glove. Thus, the use of the germicidal device requires less time than that required to change a pair of gloves and can provide cost savings by reducing the number of used latex gloves. Moreover, the device 100 would be used more frequently than a user would change gloves and therefore provide a greater degree of sanitation.

To further improve the effectiveness of sterilizing a gloved hand, an optional aspect of the present invention includes a glove coated in a reflective material to be used in conjunction with the germicidal device 100. Pathogens resting on a reflective surface, compared to those resting on a non-reflective surface, are effectively exposed to an increased level (e.g., approximately 1.5 times) of the UV-C radiation. The pathogens are not opaque, and there is a significant level of back reflected radiation. Thus, the pathogens are first exposed to the incident radiation, and then exposed to the radiation reflected by the surface on which they are resting. Since latex gloves exhibit low reflectivity and high optical loss, pathogens resting on the surface of a latex glove would be exposed to minimal reflected radiation, effectively reducing the intensity of the radiation. Therefore, according to the present invention, a glove coated in a reflective material, such as aluminum, almost doubles the UV-C absorption by the pathogens when used in germicidal device 100. The layer of reflective material does not significantly add to the cost, and does not noticeably change the flexibility/feel of the glove. The glove may be coated with the reflective material by evaporation or sputtering of the reflective material in a vacuum chamber.

Figure 4:
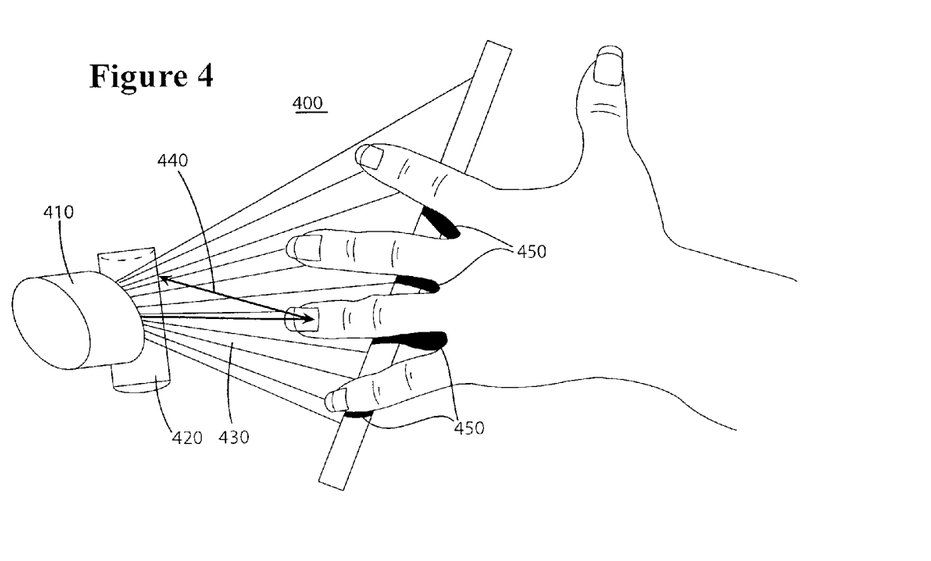
FIG. 4 illustrates a surface detector according to an aspect of a germicidal device of the present invention.

Furthermore, to ensure safe use of the germicidal device 100, in a further aspect of the present invention the device 100 can include a surface detector 400 as shown in FIG. 4. Surface detector 400 ascertains whether the bodily extremity inserted into the germicidal device 100 is covered, or has exposed bare-skin. Based on this determination, and optionally the preferences of the user, the germicidal device 100 may be configured so that the user cannot irradiate bare-skin, or so that the intensity or the duration of the radiation is reduced if bare-skin is detected.

Surface detector 400 may include a source 410, a detector 420 and a processing unit (not shown). The source 400 may be made up of a blue LED, a green LED and a red LED. The detector 420 may be made from a silicon photodiode, or any photo-detector component, and is placed on the same side of the hand as the source 410. In determining the surface of the bodily extremity, each LED is illuminated in sequence. As each LED is illuminated, the detector 420 captures the light that is reflected by the bodily extremity. Since the reflectivity properties for the different wavelengths of the three LEDs are different for various surfaces, the processing unit determines whether the surface of the bodily extremity is bare-skin or a covering material. This may be performed by comparing the strength of the captured signals to known reflectivity values for various surfaces. The arrows 430 and 440 represent the light incident and reflected by the hand. Additionally, the surface detector 400 may include indicators (not shown) to show whether or not sanitization is safe, based on whether or not the bodily extremity is covered. The indicators may include lights, or an audible signal.

UV-C radiation can be damaging to the cornea, and therefore exposure of the cornea should be avoided. Thus, because the opening 140 may not be flush with the edges of the hands or wrists inserted in the enclosure 110, some of the UV-C radiation produced by the radiation source 120 can escape the enclosure 110, and potentially irritate the cornea of the user. Thus, the germicidal device 100 can include a lid 130 that is coupled to the enclosure 110 and positioned to obstruct UV-C radiation exiting the enclosure. FIG. 1 illustrates the lid 130 as fixedly mounted to the enclosure 110. Optionally, the lid 130 can be pivotally mounted to the enclosure 110, as illustrated in FIG. 2, about a pivot mount 230, such that the lid 130 can rotate to cover the openings 140 when the germicidal device 200 is not in use.

The lid 130 can include a substance that is opaque to visible light. Alternatively, the lid 130 can be transmissible to visible light, or coated with a phosphor that produces visible light when exposed to the UV-C radiation, thereby providing indicator that the radiation source 120 is active. The lid 130 further protects objects external to the germicidal device 100, including the user's eyes, from UV-C radiation.

Figure 5:
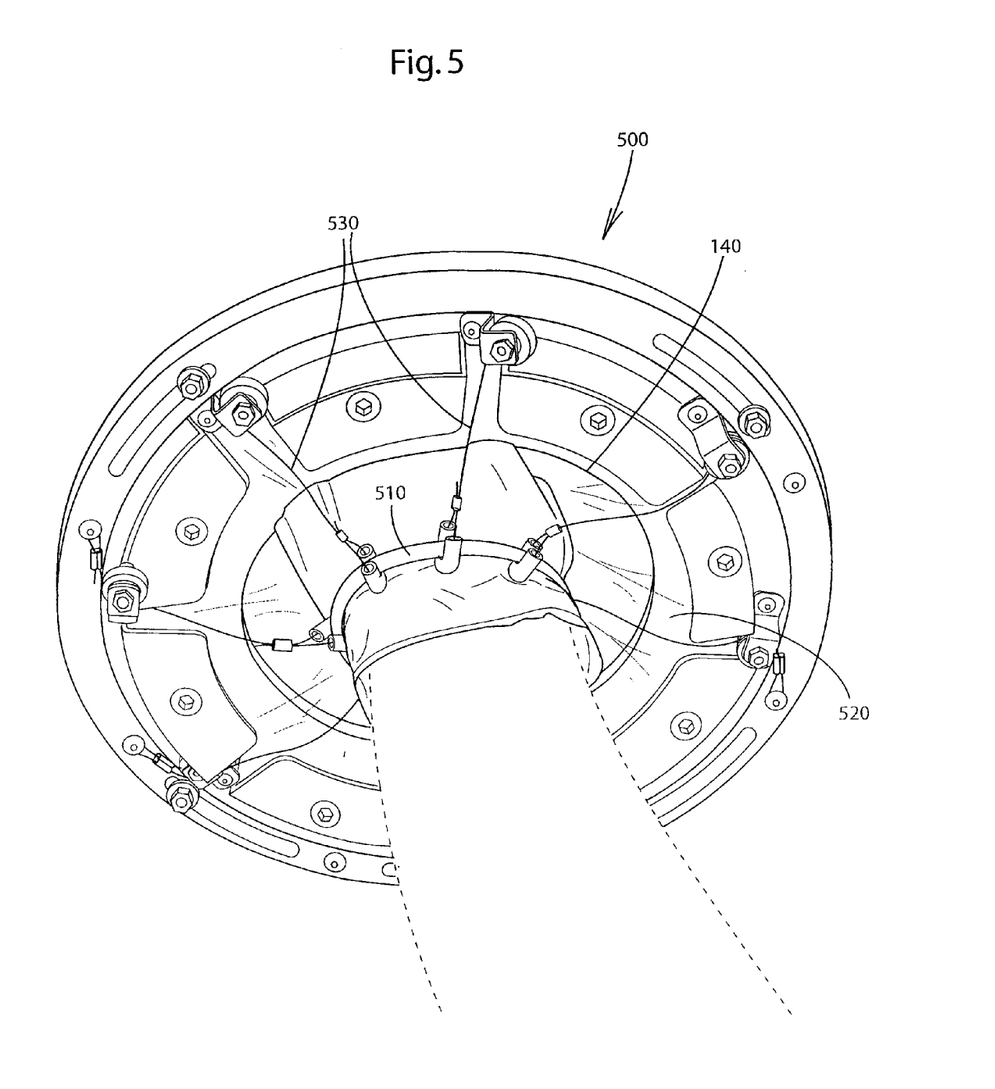
FIG. 5 illustrates a locking device according to an aspect of a germicidal device in accordance with the present invention.

Alternatively, or in addition to lid 130, the germicidal device may include a locking device 500 as shown in FIG. 5. The locking device 500 may be positioned on either side of the opening 140 of the enclosure 110. The locking device 500 has at least two positions, opened and closed, and provides at least two functions: it resists removal of the body part from being withdrawn while the radiation source is activated; and it substantially prevents UV-C radiation from escaping through the opening 140 while the body part is being sanitized or sterilized. The locking device 500 is set in the closed position when a body part is inserted into the germicidal device 100, the radiation source is activated and the body part is being sanitized or sterilized. The locking device 500 is set in the open position when the germicidal device is not is use or a user has completed sterilizing or sanitizing a body part and is attempting to withdraw the body part from the germicidal device 100. In one embodiment, the locking device 500 includes a closing ring 510, a radiation shroud 520, and retracting wires 530. The closing ring 510 may be made up of a flexible spring that is able to conform to surfaces and be stretched. When the locking device 500 is in the closed position, the closing ring 510 conforms to the inserted body part, forming a tight seal is formed around the inserted body part. In the open position, the closing ring 510 is stretched to allow the insertion and withdrawal of the body part. The radiation shroud 520 may be made up of a flexible material that is opaque to UV-C so that it prevents UV-C radiation from escaping from the germicidal device 100 through the opening 140. The retracting wires 530 are attached to the ring and are able to stretch the closing ring 510 to the open position to allow the insertion and withdrawal of the body part from the germicidal device 100.

The germicidal device 100 can be operated at low power during standby to cool the device 100 and preserve power and operating lifetime of the device and the radiation sources 120. The device can be automatically turned on to full power when the insertion of the hands is detected. Hand insertion can be detected by a sensor, the lifting of the lid 130, or by activation of the switch 160 (FIG. 2) inside the enclosure 110.

The duration of exposure (i.e., the length of time the user's hands remain in the enclosure 110) required to achieve a predefined deactivation rate depends on a number of factors including the intensity of the UV radiation produced by the radiation source 120, the proximity of the hands to the radiation source, and desired level of pathogen deactivation. Anthrax is one of the most difficult pathogens to deactivate, requiring an exposure of about 750 watts/meter$^2$ to achieve 90% inactivation.

The radiation source (i.e., lamp) power determines the intensity of the radiation. For example, a standard commercially available germicidal lamp producing 500 watts/meter$^2$ at its surface can be employed as the radiation source 120. At the external surface of a typical tubular lamp with a 2-cm diameter, an exposure of ≈750 J/m$^2$ for 90% inactivation of anthrax spores is delivered in 1.5 seconds. Thus, in order to provide 99.99% pathogen deactivation of anthrax spores the user's hands should be exposed for at least 6 seconds. Reflecting gloves reduce that time.

Lower power germicidal lamps can also be used. For example for a radiation source producing 200 watts/meter$^2$, a 2-second insertion time would produce an exposure level of at least 400 Joules/meter$^2$, which is adequate to deactivate most known pathogens by 99.99%. Alternatively, higher power lamps can also be employed thus reducing the required exposure time. One of ordinary skill in the art would understand that various implementations of the present invention are possible where the intensity of the radiation source and/or the time of exposure can be varied to achieve a desired level of radiant exposure. Further, it should be noted that because the germicidal lamps (radiation sources 120) are activated to full power for only a brief period of time, the lifespan of the tubes can be very long and the tubes can remain cool. Attention must be given to cathode circuits to minimize sputtering upon starting.

One further factor that influences the pathogen deactivation rate is the distance of the pathogen from the radiation source 120. The intensity of the exposure to UV-C radiation decreases roughly inversely as the distance from the tubular radiation source 120 increases. Thus, the enclosure 110 is preferably designed such that the extremity inserted into the enclosure 110 is in close proximity to the radiation source 120. Close proximity can be achieved by the placement of the radiation sources 120 or by creating a narrow space between radiation sources 220. Optionally, an interior barrier (not shown) that is transmissible to UV-C radiation, such as quartz-L, can be included inside the enclosure 110 to separate the radiation source 110 from the hands inserted into the enclosure 110, thereby protecting the user's hands from direct contact with the radiation source 120 and vice versa, and allowing very close exposure to the radiation sources 220.

Activation of the radiation sources 220 within the germicidal device 200 can be controlled in various ways. For example, a switch can be included in the exterior of the enclosure 110 to control power to the radiation sources 220. Alternatively, the radiation sources 220 can be controlled by pivoting the lid 130. For example a contact (not shown) between the lid 130 and the enclosure 110 can be configured to activate the radiation sources 220 when the contact is broken as the lid 130 rotates about the pivot mount 230. Alternatively, a switch 260 can be placed inside the enclosure so that the user's hands must be substantially inserted into the enclosure to trigger the switch and thereby activate the radiation sources 220. Preferably, the switch 260 is place in the interior opposite the opening 140 so as to require the user to insert a desired portion of the user's hands and wrists into the device 200.

A single switch 260 positioned properly inside the enclosure 110 can ensure an adequate level of compliance with the sanitization process. However, the user still may not insert both hands into the enclosure 110, thereby not complying with the sanitization process in full. Thus, two switches 260 can be included in the enclosure 110, wherein both switches must be triggered to activate the radiation sources 220. Preferably, the switches 260 are placed far enough apart that a user could not activate both switches 260 with one hand, but would be required to insert both hands through the openings 140 into the enclosure 110 and trigger one switch 260 with each hand. Alternatively, a barrier (not shown) can be placed between the switches 260 that would prevent a single hand from activating both switches 260.

Additional compliance mechanisms (i.e., enforced use) can be included in the system by connecting the germicidal device 200 to the surroundings of the germicidal device 200, for instance through a microprocessor control unit. For example, the germicidal device 200 can be connected to an electronic door lock, which is unlocked only after the germicidal device has completed a cycle of irradiation. Alternatively, the germicidal device can be connected to a light (e.g., a stop light) that displays red until the user activates a cycle of irradiation. Subsequently, once the cycle is complete, the light can display green as a reminder to use the germicidal device 200. Furthermore, the germicidal device 200 can be connected to an audio component that is configured to announce certain messages including a reminder to use the device, a reminder to rub the hands together, a reminder to reclaim any jewelry removed, and a thank you message after using the device.

In yet a further feature of the present invention, the germicidal device 100 can be used to deactivate pathogens in the air surrounding the enclosure 110. A blower (not shown) can be mounted to the enclosure 110 to move air through the unit. The air would receive a dose of UV-C germicidal radiation, thereby reducing the pathogen density in the surrounding space. Alternatively, convection currents created by a warm germicidal bulb (i.e. radiation source 120) can be used to increase airflow through the enclosure 110, similarly reducing the pathogens in the surrounding air. The blower can also be used to dry hands placed in the germicidal device 100.

While the invention has been described in connection with a certain embodiment thereof, the invention is not limited to the described embodiments but rather is more broadly defined by the recitations in the claims below and equivalents thereof.

We claim:

1. A germicidal system comprising:
   a UV-C radiation source configured to emit UV-C radiation having a wavelength in a range from about 235 nm to about 295 nm;
   an enclosure surrounding the UV-C radiation source, wherein:
      the enclosure comprises an opening configured to receive a bodily extremity substantially protected from exposure to UV-C radiation by a prophylactic covering substantially opaque to UV-C radiation; and
      the enclosure is configured to position the substantially protected bodily extremity such that, when the UV-C radiation source is activated, a surface of the substantially protected bodily extremity receives incident UV-C radiation having a predetermined incident intensity, wherein the incident UV-C radiation comprises at least a portion of the UV-C radiation emitted from the UV-C radiation source; and
   a device configured to activate the UV-C radiation source for a predetermined exposure time sufficient to deactivate at least 99.99% of user-specified pathogens on the surface of the substantially protected bodily extremity.

2. The germicidal system of claim 1, wherein the predetermined exposure time is calculated such that the integral of the predetermined incident intensity over the predetermined exposure time is sufficient to deactivate at least 99.99% of the user-specified pathogens on the surface of the substantially protected bodily extremity.

3. The germicidal system of claim 1, wherein the wavelength is approximately 253.7 nm.

4. The germicidal system of claim 3, wherein:
   the predetermined incident intensity is about 500 watts/m$^2$; and
   the predetermined exposure time is at least 1 second.

5. The germicidal system of claim 1, wherein the device is further configured to:
   automatically determine whether the substantially protected bodily extremity is disposed with optimal positioning;
   upon determining that the substantially protected bodily extremity is disposed with optimal positioning:
      expose the substantially protected bodily extremity to the incident UV-C radiation having the predetermined incident intensity for the predetermined exposure time; and
   upon determining that the substantially protected bodily extremity is not disposed with optimal positioning:
      not expose the substantially protected bodily extremity to UV-C radiation.

6. A germicidal system comprising:
   a UV-C radiation source configured to emit UV-C radiation having a wavelength in a range from about 235 nm to about 295 nm;
   an enclosure having an interior surface surrounding the UV-C radiation source, wherein:
      at least a portion of the interior surface is configured to substantially reflect at least a portion of the UV-C radiation emitted from the UV-C radiation source, when the UV-C radiation source is activated;
      the enclosure comprises an opening configured to receive a bodily extremity substantially protected from exposure to UV-C radiation by a prophylactic covering substantially opaque to UV-C radiation; and
      the enclosure is configured to position the substantially protected bodily extremity such that, when the UV-C radiation source is activated, a surface of the substantially protected bodily extremity receives a first incident UV-C radiation having a first incident intensity and a second incident UV-C radiation having a second incident intensity, wherein:
         the first incident UV-C radiation comprises at least a portion of the UV-C radiation emitted from the UV-C radiation source;
         the second incident UV-C radiation comprises at least a portion of the UV-C radiation reflected from the at least a portion of the interior surface; and
         the sum of the first incident intensity and the second incident intensity is a predetermined total incident intensity; and
   a device configured to activate the UV-C radiation source for a predetermined exposure time.

7. The germicidal system of claim 6, wherein the wavelength is approximately 253.7 nm.

8. The germicidal system of claim 7, wherein:
   the predetermined total incident intensity is about 500 watts/m$^2$; and
   the predetermined exposure time is at least 1 second.

9. The germicidal system of claim 6, wherein the predetermined exposure time is sufficient to deactivate at least 99.99% of user-specified pathogens on the surface of the substantially protected bodily extremity.

10. The germicidal system of claim 9, wherein the predetermined exposure time is calculated such that the integral of the predetermined total incident intensity over the predetermined exposure time is sufficient to deactivate at least 99.99% of the user-specified pathogens on the surface of the substantially protected bodily extremity.

11. The germicidal system of claim 6, wherein the at least a portion of the interior surface configured to substantially reflect at least a portion of the UV-C radiation emitted from the UV-C radiation source comprises an aluminum surface.

12. The germicidal system of claim 6, wherein the device is further configured to:
   automatically determine whether the substantially protected bodily extremity is disposed with optimal positioning;
   upon determining that the substantially protected bodily extremity is disposed with optimal positioning:
      expose the substantially protected bodily extremity to UV-C radiation having the predetermined total incident intensity for the predetermined exposure time; and upon determining that the substantially protected bodily extremity is not disposed with optimal positioning:
not expose the substantially protected bodily extremity to UV-C radiation.

13. A method for sanitizing a bodily extremity substantially protected from exposure to UV-C radiation by a prophylactic covering substantially opaque to UV-C radiation, the method comprising the steps of:
receiving the substantially protected bodily extremity into an enclosure containing a UV-C radiation source configured to emit UV-C radiation having a wavelength in a range from about 235 nm to about 295 nm;
positioning a surface of the substantially protected bodily extremity such that, when the UV-C radiation source is activated, the surface receives incident UV-C radiation having a predetermined incident intensity, wherein the incident UV-C radiation comprises at least a portion of the UV-C radiation emitted from the UV-C radiation source; and
activating the UV-C radiation source for a predetermined exposure time sufficient to deactivate at least 99.99% of user-specified pathogens on the surface of the substantially protected bodily extremity.

14. The method of claim 13, wherein the predetermined exposure time is calculated such that the integral of the predetermined incident intensity over the predetermined exposure time is sufficient to deactivate at least 99.99% of the user-specified pathogens on the surface of the substantially protected bodily extremity.

15. The method of claim 13, wherein the wavelength is approximately 253.7 nm.

16. The method of claim 15, wherein:
the predetermined incident intensity is about 500 watts/m$^2$; and
the predetermined exposure time is at least 1 second.

17. A method for sanitizing a bodily extremity substantially protected from exposure to UV-C radiation by a prophylactic covering substantially opaque to UV-C radiation, the method comprising the steps of:
receiving the substantially protected bodily extremity into an enclosure containing a UV-C radiation source configured to emit UV-C radiation having a wavelength in a range from about 235 nm to about 295 nm;
positioning a surface of the substantially protected bodily extremity such that, when the UV-C radiation source is activated, the surface receives incident UV-C radiation having a predetermined incident intensity, wherein the incident UV-C radiation comprises at least a portion of the UV-C radiation emitted from the UV-C radiation source;
automatically determining whether the substantially protected bodily extremity is disposed with optimal positioning;
upon determining that the substantially protected bodily extremity is disposed with optimal positioning:
activating the UV-C radiation source for a predetermined exposure time sufficient to deactivate at least 99.99% of user-specified pathogens on the surface of the substantially protected bodily extremity; and
upon determining that the substantially protected bodily extremity is not disposed with optimal positioning:
not activating the UV-C radiation source.

18. The method of claim 17, wherein the predetermined exposure time is calculated such that the integral of the predetermined incident intensity over the predetermined exposure time is sufficient to deactivate at least 99.99% of the user-specified pathogens on the surface of the substantially protected bodily extremity.

19. The method of claim 17, wherein the wavelength is approximately 253.7 nm.

20. The method of claim 19, wherein:
the predetermined incident intensity is about 500 watts/m$^2$; and
the predetermined exposure time is at least 1 second.

21. A method for sanitizing a bodily extremity substantially protected from exposure to UV-C radiation by a prophylactic covering substantially opaque to UV-C radiation, the method comprising the steps of:
receiving the substantially protected bodily extremity into an enclosure containing a UV-C radiation source configured to emit UV-C radiation having a wavelength in a range from about 235 nm to about 295 nm, wherein at least a portion of an interior surface of the enclosure is configured to substantially reflect at least a portion of the UV-C radiation emitted from the UV-C radiation source, when the UV-C radiation source is activated;
positioning the substantially protected bodily extremity such that, when the UV-C radiation source is activated, a surface of the substantially protected bodily extremity receives a first incident UV-C radiation having a first incident intensity and a second incident UV-C radiation having a second incident intensity, wherein:
the first incident UV-C radiation comprises at least a portion of the UV-C radiation emitted from the UV-C radiation source;
the second incident UV-C radiation comprises at least a portion of the UV-C radiation reflected from the at least a portion of the interior surface; and
the sum of the first incident intensity and the second incident intensity is a predetermined total incident intensity; and
activating the UV-C radiation source for a predetermined exposure time sufficient to deactivate at least 99.99% of user-specified pathogens on the surface of the substantially protected bodily extremity.

22. The method of claim 21, wherein the predetermined exposure time is calculated such that the integral of the predetermined total incident intensity over the predetermined exposure time is sufficient to deactivate at least 99.99% of the user-specified pathogens on the surface of the substantially protected bodily extremity.

23. The method of claim 21, wherein the wavelength is approximately 253.7 nm.

24. The method of claim 23, wherein:
the predetermined total incident intensity is about 500 watts/m$^2$; and
the predetermined exposure time is at least 1 second.

25. A method for sanitizing a bodily extremity substantially protected from exposure to UV-C radiation by a prophylactic covering substantially opaque to UV-C radiation, the method comprising the steps of:
receiving the substantially protected bodily extremity into an enclosure containing a UV-C radiation source configured to emit UV-C radiation having a wavelength in a range from about 235 nm to about 295 nm, wherein at least a portion of an interior surface of the enclosure is configured to substantially reflect at least a portion of the UV-C radiation emitted from the UV-C radiation source, when the UV-C radiation source is activated;
positioning the substantially protected bodily extremity such that, when the UV-C radiation source is activated, a surface of the substantially protected bodily extremity receives a first incident UV-C radiation having a first incident intensity and a second incident UV-C radiation having a second incident intensity, wherein:
  the first incident UV-C radiation comprises at least a portion of the UV-C radiation emitted from the UV-C radiation source;
  the second incident UV-C radiation comprises at least a portion of the UV-C radiation reflected from the at least a portion of the interior surface; and
  the sum of the first incident intensity and the second incident intensity is a predetermined total incident intensity;
automatically determining whether the substantially protected bodily extremity is disposed with optimal positioning;
upon determining that the substantially protected bodily extremity is disposed with optimal positioning:
  activating the UV-C radiation source for a predetermined exposure time sufficient to deactivate at least 99.99% of user-specified pathogens on the surface of the substantially protected bodily extremity; and
upon determining that the substantially protected bodily extremity is not disposed with optimal positioning:
  not activating the at least one UV-C radiation source.

26. The method of claim 25, wherein the predetermined exposure time is calculated such that the integral of the predetermined total incident intensity over the predetermined exposure time is sufficient to deactivate at least 99.99% of the user-specified pathogens on the surface of the substantially protected bodily extremity.

27. The method of claim 25, wherein the wavelength is approximately 253.7 nm.

28. The method of claim 27, wherein:
  the predetermined total incident intensity is about 500 watts/m$^2$; and
  the predetermined exposure time is at least 1 second.

* * * * *